United States Patent [19]

Hale et al.

[11] Patent Number: 4,761,481

[45] Date of Patent: Aug. 2, 1988

[54] SUBSTITUTED PYRIDINE DERIVATIVES

[75] Inventors: Ron L. Hale, Palo Alto; Dennis W. Solas, San Francisco, both of Calif.

[73] Assignee: Baxter Travenol Laboratories, Inc., Deerfield, Ill.

[21] Appl. No.: 712,774

[22] Filed: Mar. 18, 1985

[51] Int. Cl.[4] .................. C07D 213/68; C07D 213/65; C07D 213/73; C07D 213/55

[52] U.S. Cl. .................. 546/296; 546/297; 546/300; 546/307; 546/310; 546/311; 546/335; 424/3; 436/800

[58] Field of Search ............... 546/296, 297, 300, 307, 546/310, 311, 335; 424/3; 436/800

[56] References Cited

U.S. PATENT DOCUMENTS

| | | | |
|---|---|---|---|
| 3,753,993 | 8/1973 | Lesher et al. | 546/156 |
| 3,907,808 | 9/1975 | Lesher et al. | 260/287 R |
| 3,970,662 | 7/1976 | Carabateas et al. | 260/295.5 R |
| 4,008,239 | 2/1977 | Carabateas et al. | 260/290 P |
| 4,150,295 | 4/1979 | Wieder | 250/458 |
| 4,193,983 | 3/1980 | Ullman et al. | 424/3 |
| 4,352,751 | 10/1982 | Wieder et al. | 544/64 |
| 4,565,790 | 1/1986 | Hemmilä et al. | 436/800 |
| 4,603,209 | 7/1986 | Tsien et al. | 436/800 |

FOREIGN PATENT DOCUMENTS

0068875  6/1982  European Pat. Off. ............. 101/12

OTHER PUBLICATIONS

Pringsheim, P., Fluorescence and Phosphorescence (1949) Interscience Publishers, pp. 415-420.
Wilmott et al, Analyst, Mar. 1984, vol. 109, pp. 343-345.
Soini et al, Clin. Chem., 29/1, pp. 65-68 (1983).
Weller et al, Tetrahedron Letters, vol. 22, No. 44, pp. 4381-4384, 1981.
Weller et al, J. Org. Chem. 1982, vol. 47, pp. 4803-4806.
Boger et al, J. Org. Chem., vol. 47, No. 19, pp. 3761-3763, 1982.
Carbateas et al, J. Heterocycl. Chem., vol. II, Oct. 1974, pp. 819-821.
Martin, John C., J. Org. Chem., vol. 47, No. 19, 1982, pp. 3761-3763.

*Primary Examiner*—Mary C. Lee
*Assistant Examiner*—Dale A. Bjorkman
*Attorney, Agent, or Firm*—S. B. Fentress; P. C. Flattery; R. E. Hartenberger

[57] ABSTRACT

It is disclosed that aryl-substituted 2,6-bis[N,N-di(carboxyalkyl)aminoalkyl] pyridines in which the aryl groups are substituted with one or more electron-releasing groups are an advantageous ligand for forming fluorescent chelates with rare earth metals. The pyridine moieties can be linked to target molecules, especially biologically active target molecules to provide fluorescent tagging for use in fluoroassay techniques. The pyridine moieties are disclosed as tetraacids, as salts and as esters. Preparation processes and precursors including the corresponding aryl-substituted 2,6-dicarboxypyridines as acids, salts and esters, are disclosed as well.

24 Claims, No Drawings

SUBSTITUTED PYRIDINE DERIVATIVES

BACKGROUND OF THE INVENTION

1. Field of the Invention

This invention is in the fields of chemistry and biology and provides a fluoroassay method for use therein. More particularly, it concerns a group of aryl substituted pyridine compounds and their use as components of or as intermediates toward components of fluorescent chelate labels for fluoroassay techniques

2. Background

Fluoroassay techniques are finding increasing application in chemical, biochemical and medical analyses. Fluorescence measurement methods are intrinsically extremely sensitive However, the sensitivity of fluorescence assays, in practice, is limited by the presence of background fluorescence.

U.S. Pat. Nos. 4,150,295 and 4,058,732, issued on Apr. 17, 1979 and Nov. 15, 1977, respectively, and a chapter appearing at pages 67-80 of *Immunofluorescence and Related Staining Techniques*, Knapp, et al eds. (1978, Elsevier/North Holland Biomedical Press) disclose the general concept that background fluorescence has a relatively short life and that one can advantageously employ as measured fluorescent species, materials having a longer lived fluorescence. This work further points out that by using an intermittent excitation source and a timecoupled measurement of fluorescence one could essentially avoid or reject the background fluorescence while measuring the desired fluorescence.

Rare earth chelates have been identified by the art as materials having long-lived fluorescence. Such materials include a rare earth metal ion such as terbium or europium chelated by one or more ligands such as amine polyacids (See, U.S. Pat. No. 4,352,751 of Wieder and Wollenberg), "heteroatom-containing groups" including iminodiacetate substituted phenols, coumarins and phenanthrolines (See, Eastman Kodak European patent application No. 0068875) and aromatic diketones (See, German OLS No. 2,628,158), to point out a number of representative disclosures.

The art recognizes that the following properties are desirable in a chelating group.

1. It should form a stable chelate complex with the rare earth—i.e., with a stability constant (log K) of 17 or greater.
2. The fluorescent chelate complex with rare earth should have a long-lived fluorescence, that is, a fluorescence that is not appreciably decayed when background interference has already decayed.
3. The fluorescence excitation should occur at as long a wavelength as possible—preferably at 300 nm or greater so as to avoid interference which commonly occurs in biological samples at wavelengths of about 270 nm.
4. The fluorescent complex should have an intense emission—i.e. it should have a high quantum yield.

In addition, the materials should have solubility, chemical stability and other properties that are compatible with the nature of the samples (usually aqueous samples) with which the materials are used.

Notwithstanding this recognition in the art, the materials described heretofore generally have been at least somewhat lacking in one or more of these properties. For example, EPO No. 0068875 points out that the fluorescence of reagents such as aromatic diketones (German OLS No. 2,628,158) is quenched in water because of an "aqueous stability" problem while the phenolic aromatic ketones, coumarins and phenanthrolines (which EPO No. 0068875 specifically discloses), have exhibited a lack of chemical stability and a low quantum yield. As a result of these deficiencies no one has yet produced a widely applicable reagent system for fluoroassay techniques.

What is needed is a fluorescent chelate system that better satisfies these properties.

The present invention concerns a family of substituted pyridine derivatives as well as intermediates thereto which may be incorporated into longlived fluorescent species with rare earth metals. References to the general class of substituted pyridine derivatives include U.S. Pat. Nos. 4,008,239, 3,970,662 and 3,907,808 as well as Carbeteas and Williams, *J. Heterocycl. Chem.*, 11(5), 819 (1974); Weller and Luellen, *Tetrahedron Letters*, Vol. 22, No. 44, pp 4381-84 (1981) and Weller, Luellen and Weller *J. Org. Chem.*, 47, 4803-06 (1982). The above-noted European patent application No. 0068875 is also of interest.

STATEMENT OF THE INVENTION

We have now discovered that a 2,6-bis[N,N-di(carboxyalkyl)aminoalkyl]pyridine that is ring-substituted with a substituted aryl is a moiety which is especially attractive for use as a ligand in the formation of fluorescent chelates.

In one aspect, therefore, the present invention provides compounds which are fluorescently detectable by reason of incorporating a substituted aryl-substituted 2,6-bis[N,N-di(carboxyalkyl)aminoalkyl]pyridine moiety.

In a more particular aspect, this invention provides compounds which are fluorescently detectable by reason of incorporating a substituted aryl-substituted 2,6-[N,N-bis(carboxyalkyl)aminoalkyl]pyridine moiety which has the formula

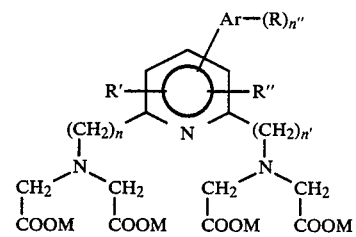

wherein n and n' are independently the integers 1 or 2, Ar is an aryl, n" is an integer equal to the number of available bonding sites on Ar, M is hydrogen or metal ion, and the n" Rs, R' and R" are each independently selected from hydrogen; electron-releasing groups including lower alkoxy, lower alkyl, amino, dialkylamino, aryl and aryloxy; and a linking group including a covalent bond and a bridge group capable of providing a link to the remainder of the molecule subject to the provisos that at least one of the n" Rs is an electron-releasing group and that at least one of R', R" and the n" Rs is a linking group to the remainder of the molecule.

The remainder of the molecule may include a biologically active material, that is, one half of a biospecific (e.g., immunologic) pair so as to permit biospecific assays to be conducted.

The invention provides compounds incorporating the above moiety which are tetraacids (i.e., M=hydrogen).

It also provides compounds which are metal salts, in particular metal complex salts wherein the four M's include one or more metal ions including rare earth metal ion so as to form fluorescent rare earth chelates.

The invention further provides as intermediates, ester corresponding to the above tetraacids, as well as precursor aryl-substituted 2,6-dicarboxypyridine compounds as diacids and as metal salts and mono and diesters thereof.

In yet another aspect, this invention provides aryl substituted pyridine tetraacid compounds as opposed to the above-noted substituted pyridine moieties. These compounds have the following formula:

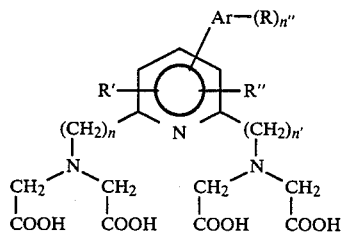

and salts thereof which also form long-lived fluorescent chelates with rare earths as well as tetra ester precursors to the tetraacids. In the formula, n and n' are integers selected from 1 and 2, R, R' and R" are the same or different groups selected from hydrogens and electron releasing groups such as lower alkoxies, lower alkyls, aminos, alkylaminos, aryls and aryloxies and the like, Ar is an aryl group, in particular a phenyl or naphthyl group and n" is an integer corresponding to the number of covalent bonding sites available on the Ar group. These pyridine tetraacid compounds form chelates with rare earth metals, preferably, europium and terbium.

The materials of this invention offer the advantage of having excitation wavelengths that are at 280 nm or greater with excitation wavelengths of 310 nm to 325 nm or greater being possible so as to avoid background interference. Prior materials that attained shifts to these wavelengths employed structures in which aromatic rings were fused to pyridine rings. When compared to these fused ring materials, the present moieties have substantially improved quantum efficiencies. In addition, the materials of this invention are chemically stable, water soluble and from highly stable metal complexes.

In yet other aspects, this invention provides an improved method for increasing the excitation wave length of fluorescent rare earth chelates which preserves high quantum efficiencies and improved methods for fluoroassay which methods involve the use of the present aromatic ring substituted pyridines as chelating ligands.

DETAILED DESCRIPTION OF THE INVENTION

The Substituted Pyridine Moieties

The substituted pyridine moieties in accord with this invention are incorporated into molecules so as to render the molecules fluorescently detectable aryl substituted 2,6-bis[N,N-di(carboxyalkyl)aminoalkyl]pyridines. The aryl substituents are themselves substituted with at least one electron-releasing group. These materials can be depicted in the following General Formula I.

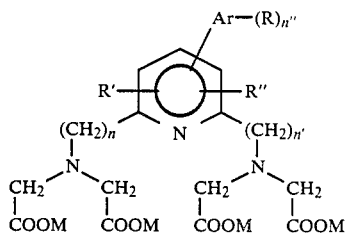

In this formula n and n' are integers, either 1 or 2 and preferably the same integer, and more preferably 1. The pyridine ring carries substituents R', R" and —Ar—(R)$_{n''}$. The R' and R" substituents may be hydrogens; electron-releasing groups such as lower alkoxies, that is 1 to 4 carbon alkoxies, especially methoxy or ethoxy; lower alkyls, that is 1 to 4 carbon alkyls such as methyls, ethyls, n and iso propyls and the like; aminos; alkyl, i.e., mono and di, and especially dialkylamino, for example, dialkylaminos wherein each of the alkyls is from 1 to 4 carbons such as dimethylamino; aryls of six carbons and aralkyls of up to about 9 carbons such as phenyls or benzyls and the like, subject to the limitation that such aryls are pendant from and not fused to the pyridine ring and aryloxies or aralkyloxies of up to about 9 carbons such as phenyloxy or benzyloxy structures; and a linking group including a covalent bond and a bridge group capable of providing a link to the remainder of the molecule as will be described.

The Ar—(R)$_{n''}$ substituent on the pyridine ring is an aryl itself containing n" R substituents. The aryl is either a phenyl or a naphthyl ring. The number n" is an integer corresponding to the number of covalent bonding sites available on the Ar substituent, i.e, 5 in the case of a phenyl or 7 in the case of a naphthyl. The R substituents on the Ar group can be selected from the same groups as the R' and R" substituents.

Thus, the Ar—R$_{n''}$ substituents can be represented structurally by the General Formulae IIa and IIb.

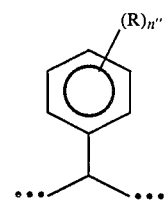

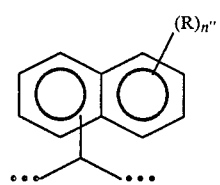

wherein

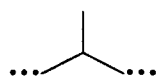

the covalent bond to the pyridine ring depending upon whether the Ar unit is a phenyl or naphthyl. Phenyl is the preferred Ar unit.

Preferred aryl-substituted pyridines can be represented in more detail by a combination structure incorporating General Formula I and one of Formulae IIa or b. This provides General Formula III

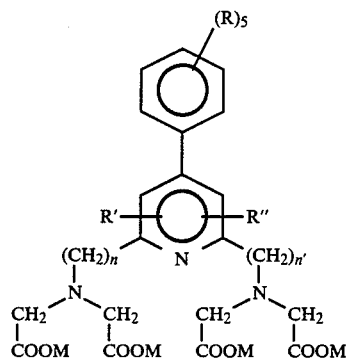

wherein R', R", the R's, M and n and n' are as previously defined. While we believe that any of the aforesaid materials will work in accord with the present invention our greatest experience is with materials having the Ar—(R)$_n$ attached to the pyridine in the 4-position, i.e., para to the pyridine nitrogen, and on that basis this relationship is preferred. Also preferred are materials wherein the linking group is one of the Rs as opposed to R' or R" and wherein one or both of R' and R" are hydrogens and especially wherein from one to three of the Rs are lower alkoxies and the rest of the Rs are hydrogen.

The aryl substituted pyridine moieties can be linked to other groups. This linking can be accomplished by a covalent bond or through some other linking group either of which constitute one of the R', R" or Rs, especially one of the Rs. This linking permits the fluorescent pyridine moieties to "tag" a biologically active biospecific group.

When the linking is accomplished through a linking group this R group should present an active or bondable site such as an amine, a hydroxyl, a carboxyl, an ester or the like to facilitate coupling of the biospecific group. Examples of such bondable R groups are the amino group (—NH$_2$) primary and secondary amine-terminated alkyls such as —CH$_2$—CH$_2$—NH$_2$ or

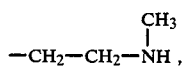

primary and secondary amine terminated aryls and aryloxies such

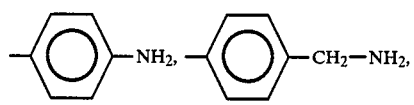

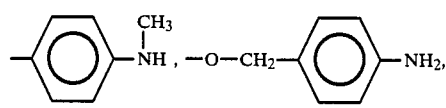

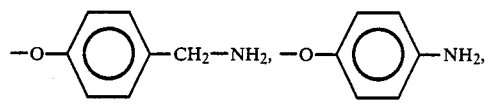

and the isomers thereof and the like; hydroxyl-containing alkyls such as —CH$_2$—CH$_2$—OH,

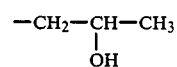

etc., and hydroxyl-containing aryls and aryloxies such as

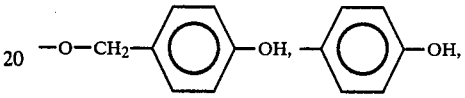

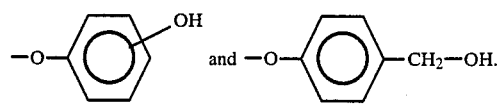

Other suitable functionalities for forming a bond to the biospecific group include amides, amidines, thioamides, ureas, thioureas, guanidines, diazos, thioethers, carboxy and phosphate esters and thioesters and other covalent linkages such as are known in the art. A preferred linking group is the simple amino group. The linking groups can couple directly to the biologically active group or can be linked through a bifunctional spacer agent such as a member of the group —CO(CH$_2$)$_4$—, —CS—, —CO(CH$_2$)$_8$NHCOCH$_2$ON=, —COCH$_2$ON=, —CO(CH$_2$)$_5$NHCO(CH$_2$)$_6$CO—, —CO(CH$_2$)$_2$SS(CH$_2$)$_2$CO—, —CSNH(CH$_2$)$_3$N(CH$_2$CH$_2$)$_2$N(CH$_2$)$_3$NHCO(CH$_2$)$_6$CO—, —CSNH(CH$_2$)$_3$N(CH$_2$CH$_2$)$_2$N(CH$_2$)$_3$NHCO(CHOH)$_2$CO—, —CSNH(CH$_2$)$_3$N(CH$_2$CH$_2$)$_3$NHCOCH$_2$ON= and the like. Such linking groups are representative and can alter and influence interactions between the fluorescent pyridine and the biospecific groups The Biospecific Group As noted above, in many advantageous applications a biologically active i.e., biospecific group is linked to the substituted pyridine The terms "biospecific group" and "biologically active group" are used in a broad sense to encompass all molecular structures which will "specifically recognize" or "specifically react" or "specifically interact" with another molecular species. Such groups can include immunologically specific groups such as antibodies and their respective antigens or haptens, hormones and their receptors, binding pairs such as the biotin avidin pair and the like. They can also include nucleic acid sequences which will specifically hybridize with their complimentary sequences.

The biospecific groups can be selected to bind with or otherwise associate with a target molecule or can be selected to mimic or to include the target molecule so as to compete with the target in the biospecific reaction.

As noted previously, the biologically active material (M$_B$) can be positioned at R' or at R" in the formulae, but preferably is linked as one of the Rs such as to give fluorescent-tagged biospecific reagents of the formula

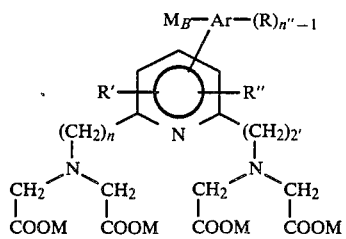

wherein $M_B$, M, n', n" are as previously described and the Rs, R' and R" are each independently selected from hydrogen; and electron-releasing groups.

Similarly, a preferred fluorescent-tagged biospecific reagent can have the formula

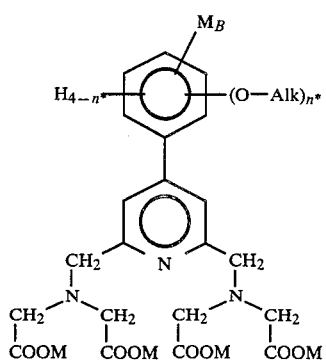

wherein M is metal ion or hydrogen, n* is an integer from 1 to 4, Alk is a 1 to 4 carbon alkyl and $M_B$ is a biologically active material.

The Target Molecule

When a biospecific group is present its target molecule or analyte may be a monoepitopic or polyepitopic material. It may be selected without limitation from materials such as drugs, metabolites, natural products, pesticides and contaminants of air and water. For purposes of illustration, one can list drugs including digoxin, digitoxin, phenytoin, theophylline, gentamicin, and tobramycin; alkaloids such as morphine, heroin, cocaine, ergot alkaloids, and the like; steroids such as the steroid hormones including estrogens and androgens for example estriol and antiinflammatory steroids for example cortisol; lactams such as the barbiturates including phenobarbital; aminoalkylbenzenes such as the amphetamines; vitamins, protaglandins such as $F_2$alpha and E, antibiotics and the like, short peptide sequences or amino acids such as thyroxine, triiodothyronine and oxytocin. Representative pollutants and pesticides include PCB, dioxin, halogenated biphenyls, carbamates, thiophosphites, phosphate esters and their metabolites. Such materials can range in molecular weight from about 50 to about 1000.

The target molecule can also be a polymeric material such as a protein or other poly(amino acid), a polynucleic acid or a polysaccharide. Such protein material can be taken from any of the classes of proteins including without limitation globulins, albumins, lipoproteins, glycoproteins, histones and the like, hypersensitive proteins including albumin, the immunoglobulins such as IgE, fibrinogen, transferrin, the various complement factors, the tumor markers like CEA (carcinoembrionic antigen) and PAP, the various blood clotting factors and protein hormones including, beta-hCG, FSH, gastrin, LH and prolactin; insulin, thyrotropin, gonadotropin and the like. Examples of biospecific polysaccharides are those derived from microorganisms such as those associated with various species of Salmonella, Streptococcus, and Klebsiella. Other targets include without limitation materials responsive to infectious disease conditions such as infection with hepatitis or rubella.

The foregoing list is intended to be a brief outline. It is to be recognized that other equivalent materials such as are listed in more detail in the art (see, U.S. Pat No. 4,193,983, columns 7–11 incorporated herein by reference) could be used in conjunction with the fluorophores provided by this invention.

Non-Linked Products

In addition to the compounds just described wherein one of the R, R' or R" groups is a link to a biospecific biologically active group, this invention also provides other materials of the same general structure of formulae I and III which do not contain a link to a biospecific material, that is where all of the R, R' and R"s are hydrogens or electron-releasing groups. Such materials especially of formulae I and III wherein M is hydrogen are useful as chelating agents for metals and when chelated to rare earth metals give a fluorescent species which can serve as an indicator for quantitative or qualitative fluorescent measurement of rare earth metal ions in solutions.

The Rare Earth Metal

The aryl-substituted pyridines of this invention form long-lived fluorescent complexes with rare earth metals including, terbium, dysprosium, europium, samarium, and neodymium, in the form of their ions. Terbium and europium ($Tb^{+++}$ and $Eu^{+++}$) are preferred rare earth metal ions.

The complexes formed between the metal ion (M) and the tetraacid ligands of this invention are generally considered to be 1:1 equimolar metal:ligand chelate complexes. They are represented structurally by the structure given as General Formula IV

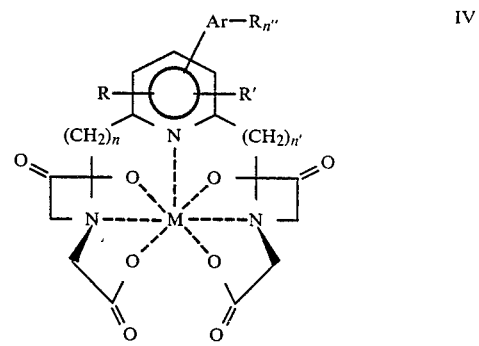

Preparative Methods

The substituted pyridines of this invention may be prepared by either of two methods. The first method is preferred if the final structure does not contain reactive amine functionalities or other functional groups incompatible with the reagents employed. The second permits such groups to be incorporated.

The first method involves

A. reacting a suitably substituted benzaldehyde or naphthaldehyde with at least two moles of 2-acyl furan to give a 1,5-di(2-furyl)-1,5-pentanedione;

B. converting the product of A to the corresponding di(furyl)pyridine by reaction with hydroxylamine in liquid phase at elevated temperature such as from 40° C. to 170° C. especially from 80° C. to 150° C.;

C. oxidizing the product of B into the corresponding pyridine-2,6-dicarboxylic acid by contact with an oxidizing agent in an organic liquid phase. An example of this oxidation is the use of an excess of potassium permanganate in an alkanol at from about 50° C. to about 100° C. for 30 to 120 minutes;

D. converting the pyridine-2,6-dicarboxylic acid to the diamide which may be carried out using an excess of oxalyl chloride followed by ammonium hydroxide at low to ambient temperature;

E. converting the diamide to the dinitrile by reaction with a dehydrating agent such as acetic anhydride, trifluoroacetic anhydride, or the like, at a temperature of from about $-10°$ to $+35°$ C.;

F. reducing the dinitrile to the diamine which may be carried out catalytically using a noble metal catalyst and molecular hydrogen in the presence of traces of acid;

G. coupling ester groups to the amine groups which may be accomplished such as by reaction with an alkylhaloacetate for example an alkyl bromoacetate in the presence of 1,8-bis(dimethylamino)naphthalene or other suitable base; and H. converting the ester groups to acids by saponification with an inorganic base such as an alkali metal carbonate or hydroxide at moderate temperature such as from about 5° C. to about 45° C. It will be appreciated that there are several separation and purification steps that are not recited but that in fact are to be carried out as well.

In preparation method 2, the first three steps are carried out essentially as in method 1 with the change that the aryl aldehyde, i.e. benzaldehyde or naphthaldehyde, carries a nitro group where an amine substituent is ultimately desired or carries another group incompatible with the subsequent reactions of method 1. The product of these three steps is a nitrophenyl or nitronaphthyl pyridine-2,6-dicarboxylic acid with various R, R' and R" substituents as may be desired and thus present on the starting materials.

In Step D of the second process the two carboxylic acid groups are selectively reduced; that is they are reduced under conditions that do not reduce the nitro group. Borane is one reducing agent that will do this. This reduction can be carried out by using an excess of borane and moderate temperatures and dry conditions. This yields the dicarbinol that corresponds to the dicarboxylic acid.

E. The dicarbinol is then reacted with a reagent that will convert the carbinol functionalities to alkyl halides. Thionyl bromide in molar excess will make this conversion at elevated temperatures such as 50° C. to 125° C., to give a product which is the desired nitroaryl pyridine subtituted in the 2 and 6 positions relative to the pyridine nitrogen with alkyl bromides.

F. In this step the alkyl bromide substituted pyridine is reacted with an iminodiacetic acid diester to replace the two bromide groups with iminodiacid functionalities. This may be carried out using a base like 1,8-bis(-dimethylamino)naphthalene and a moderate temperature such as from about 25° C. to about 55° C. and an inert atmosphere. This gives the tetraester.

G. The four ester groups can then be removed such as using the saponification conditions shown in step H of Method 1.

H. In the final step of this method the nitro group on the aryl substituent is reduced to an amine. This can be carried out catalytically using a noble metal catalyst and molecular hydrogen. Representative catalysts include platinum or palladium on alumina or carbon. Hydrogen pressures can range from about atmospheric to a few atmospheres, i.e. 1-10 atmospheres; and temperatures from about ambient to about 75° C. are generally employed to achieve the desired selective reduction. This provides the desired amine substituted pyridine material. Other equivalent preparation processes can be employed if desired. For example, an amine functionality can be introduced by a modification of process 1 wherein the product of step G is nitrated with fuming nitric acid and the nitro group so introduced is thereafter reduced as in process 2.

Intermediates

In these processes several key intermediates are produced which are believed to be new compounds. These include the 2,6-dicarboxylic acid-substituted pyridines which could exist as acids, salts or as mono or diesters with a formula

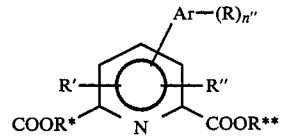

wherein Ar is an aryl, n" is an integer equal to the number of available bonding sites on Ar; R, R' and R" are independently selected from hydrogen, electronreleasing groups including lower alkoxy, lower alkyl, amino, dialkylamino, aryl and aryloxy; and linking groups; and R* and R** are independently selected from among metal ions, hydrogens and lower alkyls.

Use of the Products

The products of this invention have broad utility as ligands for chelating rare earth metals. The chelates so formed are fluorescent and thus provide a method for measuring rare earth ion content of materials. The substituted pyridines described herein are particularly useful as their rare earth metal chelates in a variety of assay procedures where their fluorescent properties allow them to serve as labels for biospecific molecules. Typically, a ligand or chelate of this invention is prepared having a reactive functional group such as an isothiocyanate, amine, imidate, diazo or other suitable group which is reacted with a suitable reactive group of a biospecific molecule such as an antibody, antigen, hapten or other target molecule. The thus labeled member of a binding pair of biospecific molecules may be used in any of a variety of assay methodologies known to those skilled in the art including competitive binding assays and immunometric, sandwich-type assays.

EXAMPLES

This invention is further described by the following examples. They are intended to exemplify the invention and are not to be considered as limiting its scope.

EXAMPLE 1

Preparation of

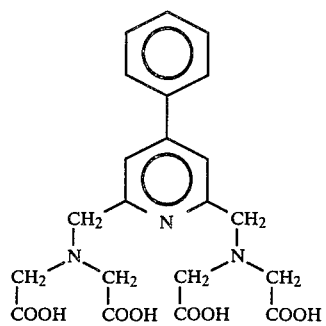

A. Preparation of 5-di(2-furyl)-3-phenyl-1,5-pentanedione

| Benzaldehyde | 62.6 g (60 ml) (0.59 mols) |
| --- | --- |
| 2-Acetyl Furan, 85% | 165 g (150 ml) (1.27 mols) |
| Potassium Hydroxide, 85% | 35 g (0.53 mols) |

The KOH is dissolved in methanol (about 600 ml) with heating and stirring. The solution is cooled slightly and a mixture of the aldehyde and furan is added all at once. The mixture is heated to 60° C. and stirred for 45–60 min. Initially a green tint develops which rapidly darkens to brown. The reaction mixture solidifies to a mass of orange-brown crystals. Ethanol is added (about 150 ml) and the solid is broken up. The mixture is chilled overnight and the product crystals are recovered by filtration and washed with ice cold ethanol (about 400 ml), followed by a pentane wash (about 200 ml). The crystals are dried in vacuo at 80° C. Yield of pentanedione, 103.5 gms or 57.3%.

B. Preparation of 4-Phenyl-2,6-di(2-furyl) pyridine

| 1,5-Di(2-furyl)-3-phenyl-1,5-pentaedione | 143 g | |
| --- | --- | --- |
| Hydroxylamine hydrochloride | 129 g | Aldrich 102337 |
| n-Butanol | 1600 ml | Sigma 13F-5070 |

The "dione", as produced in step A and a repeat thereof, the hydroxylamine and the butanol are combined in a 5-liter 3-neck flask fitted with mechanical stirrer and condenser and refluxed and stirred for 5 hrs, cooled and stirred for about 60 hours. The resulting black solution is poured into 2 l of 15% NaOH and extracted with toluene (1 l). The organic layer is washed with deionized water (1×200 ml), dried over $Na_2SO_4$, and concentrated on a rotary evaporator. The thick residue is taken up in $CH_2Cl_2$ (about 250 ml). Hexanes (about 250 ml) are added to the resulting solution which is filtered through silica gel and eluted with 1:1 $CH_2Cl_2$/hexanes (about 500 ml). The filtrate is concentrated, ethanol (about 200 ml) is added and the mixture is cooled in ice. Filtering the resulting crystals and washing with ice cold ethanol (about 200 ml) and drying in vacuo at ambient temperature, yields a first crop of crystals of about 65 grams. The filtrate is concentrated, purified and cooled to give a second crop of 13.6 g of crystals.

C. 4-Phenyl-2,6-pyridinedicarboxylic acid

The difuryl pyridine product of step B. is oxidized with permanganate.

| Product of Step B | 23 mmoles |
| --- | --- |
| $KMnO_4$ | 45.4 grams |
| t-butanol | 1500 ml |
| water | 300 ml |

The butanol (about 1 liter) is placed in a 3-neck flask fitted with a mechanical stirrer, mantle and condenser. The product of step B is added and rinsed into the flask with the remaining t-butanol. The mixture is heated and stirred until solution results; then the $H_2O$ is added and when the temperature reaches about 75° C. the $KMnO_4$ is added in portions over about 30 minutes. The mixture is refluxed for 90 minutes. Alcohol is distilled off with aspirator vacuum and the hot residue is filtered through Celite ® and washed with hot 1:1 t-BuOH/$H_2O$. Any residual $KMnO_4$ is consumed with $NaHSO_3$ and the solution is concentrated to about 150 ml on a rotary evaporator (about 65° C.). After acidifying with 2N HCl (25 ml) the resulting crystals of the desired 4-phenyl-2,6-pyridinedicarboxylic acid are filtered, washed and dried.

D. 4-Phenyl-2,6-pyridinedicarboxamide

| 4-Phenyl-2,6-pyridine-dicarboxylic acid | 21.5 mmoles |
| --- | --- |
| Oxalyl chloride | 4.8 ml |
| Methylene chloride | 80 ml |
| Dimethylformamide | 5 drops |

The pyridinedicarboxylic acid is added to a 100 ml 2-neck flask with the $CH_2Cl_2$, DMF and a stir bar. The flask is closed with a $CaSO_4$ drying tube, and cooled in ice. Then the oxalyl chloride is added over about 5 minutes from a syringe and stirred for about 2 hours at room temperature. The resulting solution is concentrated on a rotary evaporator to give the solid acid chloride; benzene (150 ml) is added and removed by rotary evaporator and the residue is vacuum dried. The acid chloride is added to $NH_4OH$, 28%, (50 ml) over 5–10 minutes with stirring, stirred for an hour, filtered and washed with water and dried to give the desired amide.

E. 4-Phenyl-2,6-pyridinedicarbonitrile

| 4-Phenyl-2,6-pyridine-dicarboxamide | 17.5 mmoles |
| --- | --- |
| p-Dioxane | 170 mls |
| Pyridine | 11.3 ml |
| Trifluoroacetic anhydride | 11.0 ml |

The first three ingredients are combined in a 250 ml flask with a stir bar. The flask is closed under argon, cooled in ice until frozen dioxane is present (10°). The anhydride is added over about 10 minutes (temp about 15° C.) and the mixture is stirred for two hours at room temperature. The resulting dark solution is poured into water and then extracted thrice with 150 ml portions of methylene chloride. The extracts are dried over Na₂SO₄ and concentrated on the rotary evaporator to a dark solid which is then taken up in methylene chloride and eluted through silica with additional methylene chloride. The eluent is concentrated to a solid and dried to give the desired dicarbonitrile.

F. 4-Phenyl-2,6-di(aminomethyl)-pyridine

| 4-Phenyl-2,6-pyridine-dicarbonitrile | 13.5 mmoles |
| Ethanol with 2% HClO₄ | 370 ml |
| 10% Palladium on carbon | 3.7 g |

The nitrile is suspended in the ethanol to which 10.5 ml of 70% HClO₄ has been added and the mixture transferred to a Parr bottle. The bottle is purged with nitrogen and the catalyst is added. The bottle is then pressured to 40 psi with hydrogen. After 30 minutes, the bottle is opened and the liquid recovered and concentrated to a dark liquid. A yellow solid is recoved by adding the liquid to diethyl ether and filtering. The perchlorate salt solid is dried on a vacuum pump. This amine perchlorate is then dissolved in about 30 ml of water and added to 40% NaOH. The liberated amine that results is extracted with CH₂Cl₂, dried over Na₂SO₄ and concentrated to a dark oil on a vacuum pump.

G.
4-Phenyl-2,6-bis[N,N-di(methoxycarbonylmethyl)aminomethyl]-pyridine

| Amine of Step F | 12.0 mmole |
| 1,8-bis(dimethylamino)-naphthalene | 10.3 g |
| Methyl Bromoacetate | 7.35 g |
| Acetonitrile | 130 ml |

The base is placed in a flask. The amine is taken up in acetonitrile and placed in the flask with it. A stir bar is added and the mixture is stirred at 45° C. until it is homogeneous. Then the methyl bromoacetate is dripped in in 40 ml of acetonitrile with the system under argon. After about 16 hours, at about 45° C. the product is poured into 150 ml of water and 1.5 ml of 0.1M citric acid. This mixture is then extracted with methylene chloride. The extracts are washed, dried, concentrated, redissolved and filtered through silica. The product is purified by silica gel chromatography using ethyl acetate/methylene chloride as solvent.

H. Saponification of Tetraester

The tetraester of Step G is saponified by placing it in methanol/water, 1:1, and adding a molar excess of K₂CO₃ and stirring at room temperature for 2.5 hours. Then the solution is acidified to pH 7, and dried to give the desired tetraacid, the identity of which is confirmed by NMR.

EXAMPLE 2

The preparation of Example 1 is substantially repeated with the change that in Step A an equivalent amount of 2,4-dimethoxybenzaldehyde is substituted for the benzaldehyde such that the intermediate formed is 4-(2,4-dimethoxyphenyl)-2,6-pyridinedicarboxylic acid and the final product is the 2,4-dimethoxy analog of the product of Step H of Example 1. The yields obtained for several of the various steps are as follows
Step A 95%
Step B 72%
Step E 84% of the desired product, 4-(2,4-dimethoxyphenyl)-2,6-bis[N,N-di(carboxymethyl)aminomethyl]-pyridine

EXAMPLES 3–17

The preparation of Example 1 is substantially repeated fifteen times with the change that the benzaldehyde is replaced with an equivalent molar amount of the following substituted benzaldehydes:

| Example No. | Benzaldehyde Analogue |
| --- | --- |
| 3 | 4-methoxy benzaldehyde |
| 4 | 3,4-dimethoxy benzaldehyde |
| 5 | 3,4,5-trimethoxy benzaldehyde |
| 6 | 2,5-dimethoxy benzaldehyde |
| 7 | 2,4,5-trimethoxy benzaldehyde |
| 8 | 4-ethoxy benzaldehyde |
| 9 | 2,4-dipropoxy benzaldehyde |
| 10 | 2-ethoxy-4-methoxy benzaldehyde |
| 11 | 4-benzyloxy |
| 12 | 3-methoxy-4-benzyloxy |
| 13 | 3,4-methylenedioxy |
| 14 | 2-methoxy-4-benzyloxy |
| 15 | 2,4-dimethoxy |
| 16 | 2,4,6-trimethoxy |
| 17 | 3-methoxy-4-(4-nitrobenzyloxy) |

With these different benzaldehydes the corresponding 2,6-pyridinedicarboxylic acid intermediates and tetraacid final products are achieved.

EXAMPLE 18

This Example shows the introduction of amine substituents onto the phenyl ring. Steps A, B, and C of Example 1 are repeated with the change that in place of the benzaldehyde, an equimolar amount of 3-nitrobenzaldehyde is used. This provides 4-(3-nitrophenyl)-2,6-pyridinedicarboxylic acid.

D. 4-(3-Nitrophenyl)-2,6-pyridinedimethanol

| Diacid as above | 28.8 g (0.1 moles) |
| Borane/THF Complex | 288 ml, 1 molar |

The diacid is placed in a dry 2 l flask with 1000 ml of THF and a stirring bar. A drying tube is set up and the flask is blanketed in argon. The borane/THF complex is then added gradually over 20–30 minutes with vigorous stirring at room temperature. The stirring is continued for four hours and then the excess borane is hydrolyzed with dilute HCl (20 ml of 6N and 85 ml of H₂O). Then 60 ml of 10% Na₂CO₃ is added and the solution is concentrated on a rotary evaporator. The residue is added to aqueous bicarbonate and extracted three times with ethyl acetate, the extracts are dried and stripped to obtain the desired diol as an orange solid.

E. 4-(3-Nitrophenyl)-2,6-bis(bromomethyl)pyridine

| Diol of Step D | 9.1 g (35 mmol) |
| Thionyl bromide | 7.0 ml (90 mmol) |

The diol of Step D is placed in a flask and about 20 ml of methylene chloride is added followed by the thionyl bromide. The flask is closed with an inlet adaptor and placed in an oil bath at 80° C. The methylene chloride and HBr are vented and a viscous residue remains. This is placed in aqueous $Na_2CO_3$ and extracted thrice with methylene chloride. The extracts are dried, concentrated, diluted with methylene chloride and filtered through silica. The filtrate is collected and evaporated to give the desired dibromide.

F.
2,6-bis[N,N-di(carboxymethyl)aminomethyl]-4-(3-nitrophenyl)-pyridine tetramethyl ester

| | |
|---|---|
| Dibromide of Step E | 3.44 g (8.9 mmol) |
| Iminodiacetic acid dimethyl ester | 2.88 g |
| 1,8-bis(dimethylamino)-naphthalene | 3.76 g |
| Acetonitrile | 140 ml |

The base is placed in a flask. The iminodiester is mixed with the acetonitrile and added. The flask is blanketed with argon and heated to 45° C. Then the dibromide, in solution in THF, is added over 60–90 minutes with magnetic stirring. After 18 hours the mixture is cooled and stirred at room temperature for about two days. The mixture is added to benzene, filtered, washed with 0.1M citric acid and water and dried over $Na_2SO_4$. The solution is then concentrated to an oil, taken up in methylene chloride and passed though silica gel twice with ethyl acetate/methylene chloride followed by ethyl acetate as eluent. Fractions are taken and the desired material is isolated and concentrated to an amber oil.

G. Reduction of Nitro Group to Amine

| | |
|---|---|
| Nitrotetramethyl ester of Step F | 2.7 g (4.94 mmole) |
| 5% Palladium on carbon | 2.7 g |
| Ethyl Alcohol | 300 ml |

The nitro compound is placed in a 1 liter flask with 300 ml ethanol. The flask is purged with nitrogen and the catalyst is added. The flask is then pressured to 1 atm with hydrogen. After 1 hr the reaction mixture is filtered and the filtrate concentrated to a yellow oil via rotary evaporation. The oil is determined to be the aminotetramethyl ester corresponding to the product of Step F.

H. Saponification

The ester groups of the aminotetramethyl ester of Step G are saponified using the method of Example 1. This yields the desired 3-aminotetraacid.

EXAMPLE 19

A. Preparation of 2,6-bis[N,N-di(carboxymethyl)aminomethyl]-4-(4-nitrophenyl)-pyridine tetramethyl ester Fuming nitric acid (0.03 ml, 0.4325 mmol) is added at room temperature to a solution of trifluoromethanesulfonic acid in methylene chloride (4 ml). After stirring for 5 minutes, a solution of 2,6-bis[N,N-di(carboxymethyl)aminomethyl]-4-phenyl-pyridine tetramethyl ester such from step G of Example 1 (86 mg, 0.173 mmol) in a small amount of methylene chloride is slowly added at 0° C. The solution is allowed to warm to room temperature and stirring is continued for one hour. The reaction mixture is then poured onto ice and the mixture is neutralized with sodium carbonate. Extraction with methylene chloride followed by drying over sodium sulfate and evaporation gives 90 mg of crude product.

B. Preparation of 2,6-bis[N,N-di(carboxymethyl)aminomethyl]-4-(4-aminophenyl)-pyridine tetramethyl ester The crude product from the above reaction (90 mg, 0.17 mmol) is dissolved in ethanol (13 ml), 50 mg of 10% Pd/C is added and the mixture is stirred at room temperature under one atmosphere of hydrogen for one hour. The catalyst is removed by filtration and the solvent evaporated to give 60 mg of the 4-amino compound. The 3-amino compound (51 mg) is prepared similarly from 70 mg (0.129 mmol) of the corresponding 3-nitro compound which had been prepared via preparation method 2. This preparation is substantially as shown in Example 18. If desired these or similar aryl pyridines having amine substrates on their aryl rings can be reacted with thiophosgene under conditions known for the reaction of theophosgene with aryl amines to convert the amine to an isothiocyanate which in turn can couple to amine-containing target molecules or the like.

C. Conjugation of 2,6-bis[N,N-di(carboxymethyl)aminomethyl]-4-(4- and 3-aminophenyl)-pyridine tetramethyl esters to theophylline-8-butyric acid Isobutylchloroformate (0.02 ml, 0.117 mmol) is added to a solution of theophylline-8-butyric acid (31.3 mg, 0.117 mmol) in dimethylformamide (1.5 ml) containing triethylamine (0.20 ml, 0.117 mmol) at 0° C. under an argon atmosphere. After 0.5 hour at 0° C., a solution of the 4-amine (60 mg, 0.117 mmol) in chloroform is slowly added. The solution is stirred for 17 hours at 0°–5° C. and then the solvents are removed by evaporation to leave 103 mg of crude product. The material is chromatographed on silica gel with chloroform:methanol (9:1) and on reverse phase C-18 silica gel with methanol:water (7:3) to give 60 mg (67% yield) of the desired product. The corresponding 3-amino compound (51 mg, 0.01 mmol) is treated similarly to give 50 mg of material having the theophylline derivative conjugated at the 3-position.

D. Preparation of 2,6-bis[N,N-di(carboxymethyl)aminomethyl]-4-[4-(theophylline-8-butyramido)-phenyl]-pyridine tetraacid The tetramethyl ester (34 mg, 0.045 mmol) from the previous step is dissolved in methanol (2 ml) containing 0.2 ml of 1N sodium hydroxide and heated at reflux for three hours. The solution is then cooled in an ice bath and acidified with 1N HCl and evaporated to give the crude product. Purification via reverse phase column chromatography in methanol:water (6:4) gives 14 mg of the tetraacid. Saponification of 40 mg (0.05 mmol) of the analogous 3-substituted compound gives 14.6 mg of its tetraacid after reverse phase chromatography.

E. Preparation of Chelates

The tetraacids of Part D are separately dissolved in 0.01M sodium borate solution to a concentration of $10^{-5}$M. Then an equivalent molar amount of aqueous terbium chloride is added to each and the mixtures are allowed to stand for a few minutes. Fluorescence measurements are carried out and demonstrate that 1:1 molar chelate complexes of the tetraacids and the terbium have been formed and that such complexes are fluorescent and stable.

F. A homogeneous fluoroimmunoassay for theophylline by enhancement of fluorescence on binding of labelled theophylline to antibody An assay for theophylline is carried out by allowing the terbium chelate of the fluorophore-labelled theophylline tracer above (i.e., 2,6-bis[N,N-di(carboxymethyl-)aminomethyl]-4-[4-(theophylline-8-butyramido)-phenyl]-pyridine terbium chelate) to compete with theophylline standards for binding to antitheophylline antibody. The labelled theophylline on binding to antibody undergoes an enhancement of its fluorescence and this enhancement is proportional to the amount of labelled theophylline bound and inversely proportional to the amount of theophylline present in the sample. The assay is carried out in polystyrene tubes (12×15 mm) to which 1 ml of pH 8.5 0.01M sodium borate buffer was added. This is followed by the addition of 10 ul of 1 $\mu$M tracer (8.7 ng) and 10 $\mu$l of theophylline standard (0, 5.4, 16.2, 54, and 540 ng). Addition of 25 ul of about 0.3 $\mu$M anti-theophylline antibody in 0.01M borate containing 0.1M sodium chloride and 1% normal human serum (final concentration in assay tube about 7.5 nM) leads to increases in the observed fluorescence of 400%–50%, respectively, for the various standards. This corresponds to B/B$_o$ values of 80, 64, 53 and 14% for the 5.4, 16.2, 54 and 40 ng standards, respectively.

EXAMPLE 20

A. Preparation of 0-benzyl vanillin

| Vanillin | 100.4 g (0.66 mols) Aldrich |
| --- | --- |
| Benzyl chloride | 84.0 gms (77 ml; 0.66 mols) |
| Potassium carbonate | 115 gms |
| Acetone | 2 l |
| 18-Crown-6 | 3 gms |

The above materials are combined in a 3-liter 3-necked round bottomed flask fitted with a mantle, condenser and mechanical stirrer. The mixture is stirred at reflux for 70 hrs. It becomes light yellow during the first 24 hours and turns to light tan by the third day at reflux. About 1 liter of acetone is then distilled off and the residue is poured into crushed ice (about 2 liters), and water (about 500 ml) with stirring. The solution is seeded to give a solid precipitate which is allowed to stand about 20 minutes then filtered, washed with EtOH (0° C., 400 ml) and dried in vacuo to give 120 g of the desired product which represents a yield of about 75%.

B. 2,6-di(2-furyl)-4-(3-methoxy-4-benzyloxyphenyl)-pyridine

| O—Benzyl vanillin (From Part A) | 31.5 g (0.13 mols) |
| --- | --- |
| Acetyl furan | 43 g (0.39 mols) Aldrich |
| Methanol | 300 ml |

The above materials are combined in a 500 ml flask and heated and stirred at about 55° C. until homogeneous (about 20 mins). Then about 5 ml 20% KOH/MeOH is added and heating and stirring are continued for 45–60 min. Then another 15 ml of 20% KOH/MeOH is added, the flask mouth is lightly covered and the contents are heated and stirred for about 16 hrs. The product is acidified with 6N HCl (about 10 ml) and concentrated on a rotary evaporator at about 55° C.

Then, hydroxylamine hydrochloride 22 gms, and n-butyl alcohol 250 ml are added and the mixture is refluxed for 3 hrs using a mantle. The butanol is removed on a rotary evaporator at about 65° C. and the residue is poured into water (about 200 ml), basified with 6N NaOH (60 ml) and extracted with toluene (2×200 ml). The extracts are washed with H$_2$O (about 100 ml), dried over Na$_2$SO$_4$ and concentrated on the rotary evaporator at about 65° C. to a black oil. This is filtered through silica gel (about 200 g) and eluted with 1:1-CH$_2$Cl$_2$/hexanes (about 1 liter). The eluent is concentrated to an oil. The oil is again subjected to silica filtration, concentrated again to an oil and yet again filtered through silica (about 200 gms) this time eluting with toluene/CH$_2$Cl$_2$—9:1 (about 1 liter). This eluent is concentrated to an amber oil which is dissolved in EtOH (about 50 ml) and again concentrated to an oil. Product yield is about 25 gms.

C. 4-(3-Methoxy-4-benzyloxyphenyl)-2,6-pyridinedicarboxylic acid

| Difuryl pyridine (From Part B) | 19 g (0.045 mols) |
| --- | --- |
| t-Butyl alcohol | 3 l |
| DI water | 0.6 l |
| Potassium permanganate | 93 gms |

The procedure of Part C of Example 1 is followed with the following changes: After KMnO$_4$ addition, the mixture is heated and stirred for 1½ hrs. Then the t-BuOH is distilled off. After concentrating to about 200 ml, the product is acidified with 2N HCl (about 50 ml). A canary yellow precipitate forms which is thinned with a few ml of water, filtered and washed with cold water (about 50 ml) and dried in vacuo to give 15.2 gms of product which is about 90% yield.

D. 4-(3-Methoxy-4-benzyloxyphenyl)-2,6-pyridinedicarboxylic acid chloride

| Diacid (from Part C) | 6.07 g (0.016 mols) |
| --- | --- |
| Methylene chloride | 60 ml |
| Oxalyl chloride | 3.5 ml |
| Dimethylformamide | 4 drops |

The diacid is weighed into a 100 ml 2-neck round bottom flask that is fitted with a drying tube and septum stopper. A stir bar is added along with the CH$_2$Cl$_2$ (about 60 ml) and 4 drops DMF. The mixture is stirred in ice while the oxalyl chloride (3.5 ml) is slowly added from a syringe (addition time about 5 min.). Then the reaction mixture is stirred at room temperature for 2 hours. The acid passes into solution in about 1 hour with evolution of HCl. The dark solution is transferred to a 250 ml flask and solvent is removed on a rotary evaporator. Benzene (about 100 ml) is added to the yellow residue and removed on the rotary evaporator to obtain 6.65 grams of dark green solid which is the desired chloride.

E. 4-(3-Methoxy-4-benzyloxyphenyl)-2,6-pyridinedimethanol

| Diacid chloride (From Part D) | 6.65 g (0.016 moles) |
| --- | --- |
| Diglyme | 300 ml |
| Sodium borohydride | 1.5 gms |
| Tetrahydrofuran | 20 ml |

The NaBH$_4$ is weighed into a dry 500 ml 3-neck flask fitted with an argon inlet, thermometer and addition funnel. A stir bar and diglyme (about 300 ml) are added and the flask is purged with argon and cooled to 0° C. The diacid chloride is dissolved in diglyme (about 40 ml) and THF (about 20 ml), transferred to the addition funnel and added dropwise to the flask with stirring and cooling over about 15 minutes (temperature 0° C.). The mixture is stirred at room temperature for 2 hours. Solution color changes from amber to coral during first hour then fades to a turbid tan over next hour. The product is poured into water (about 500 ml) and about 100 ml of 0.1M aqueous citric acid and concentrated on a rotary evaporator (60° C.). The residue (about 500 ml) is poured into water (about 1 liter) and extracted with Et$_2$O (4×100 ml). The extracts are dried over Na$_2$SO$_4$ and concentrated on a rotary evaporator to give 4.0 gms of the desired diol as a tan solid that is soluble in DMSO.

F. 4-(3-Methoxy-4-benzyloxyphenyl)-2,6-di(bromomethyl)-pyridine

| Diol (Of Part E plus a repeat) | 5.1 g (21.1 mmoles) |
| --- | --- |
| Triphenylphosphine | 15.2 g |
| Bromine | 3.0 ml |

The phosphine is weighed into a dry 250 ml 3-neck round bottomed flask. CH$_3$CN (about 50 ml) and a stir bar are added and the flask is closed with a septum and argon inlet. The solution is cooled to 0° C. in ice/MeOH and Br$_2$ is dripped in over about 20 minutes. The mixture is stirred at room temperature for 15 minutes. The diol is suspended in CH$_3$CN (about 75 ml)., transferred to the phosphine-bromine complex, stirred for 2 hours at room temperature and poured into water (about 600 ml) followed by saturated NaHCO$_3$ (about 150 ml). This aqueous suspension is then extracted with CH$_2$Cl$_2$ (2×200 ml). The extracts are dried over Na$_2$SO$_4$, filtered through silica gel eluting with CH$_2$Cl$_2$. The eluents are concentrated on a rotary evaporator to 2.2 grams of a white solid which is the desired dibromide and contains traces of triphenylphosphine oxide.

G. 2,6-bis[N,N-di(carboxymethyl)aminomethyl]-4-(3-methoxy-4-benzyloxyphenyl)-pyridine tetramethyl ester

| Dibromide(From Part F) | 2.15 g (4.5 mm) |
| --- | --- |
| Iminodiacetic acid dimethyl ester | 1.45 g (9.0 mm) |
| 1,8-bis(dimethylamino)-naphthalene | 1.94 g |

The iminoester is weighed into a dry 100 ml 3-neck flask and the base and CH$_3$CN (about 50 ml) are added. The dibromide is dissolved in THF (about 35 ml) and added to the flask with stirring under argon at 45° C. overnight. The reaction mixture is poured into water (about 150 ml) and 0.1M citric acid (about 150 ml) and EtOAc (about 150 ml). The EtOAc layer is separated; washed with 0.1M citric acid (about 100 ml), water (about 100 ml) and brine (about 100 ml; dried over Na$_2$SO$_4$; and concentrated to a thick purple oil. The oil is dissolved in CH$_2$Cl$_2$ and plug filtered through silica (35 gms). A purple band is eluted with 10% EtAc in CH$_2$Cl$_2$ (about 200 ml). Then the desired tetraester is eluted with 50% EtAc/CH$_2$Cl$_2$ (200 ml) and 80% EtAc/CH$_2$Cl$_2$ (about 200 ml). The eluent fractions containing the tetraester are concentrated to about 2.5 grams of oil.

H. Saponification of Tetraester

The tetraester of step G is saponified using the procedure of Example 1 to give the desired tetraacid.

EXAMPLE 21

Following the general procedures of Example 19, the 4-[4 (or 3)-aminophenyl]-2,6-bis[N,N-di(carboxymethyl)aminomethyl]-pyridine tetraesters are coupled to digoxigeninone-3-O-carboxymethyloxime, phenytoin-3-(8-octanoic acid) and cortisol-3-O-carboxymethyloxime to give the conjugated materials. Saponification of the tetraesters gives the tetraacids which, with rare earth metals, formed fluorescently tagged, immunologically active analogs of the target analytes.

We claim:

1. A fluorescently detectable molecule characterized as comprising a substituted aryl-substituted 2,6-bis(N,N-di(carboxyalkyl)aminoalkyl)pyridine moiety wherein at least one of the substituents present on the aryl is an electron-releasing group and wherein at least one of the substituents present in the aryl as a substitute on the pyridine provides a binding group for attachment to other molecules.

2. The fluorescently detectably molecule of claim 1 additionally comprising a biologically active material attached through the linking group.

3. The fluorescently detactable molecule of claim 1 wherein said electron-releasing groups are selected from among lower alkoxies, lower alkyls, aminos, dialkylaminos, aryls and aryloxys.

4. The fluorescently detactable molecule of claim 1 wherein said substituted aryl-substituted 2,6-bis[N,N-di(carboxylalkyl)aminoalkyl]pyridine moiety has the formula

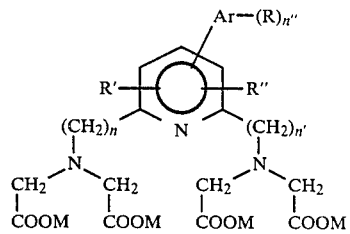

wherein n and n' are independently the integers 1 or 2, Ar is an aryl, n" is an integer equal to the number of available bonding sites on Ar, M is hydrogen or metal ion, and the n" Rs, R' and R" are each independently selected from hydrogen; electron-releasing groups themselves selected from lower alkoxy, lower alkyl, amino, dialkylamino, aryl and aryloxy; and a linking group including a covalent bond and a bridge group capable of providing a link to the remainder of the molecule subject to the provisos that at least one of the n" Rs is an electron-releasing group and that at least one of R', R" and the n" Rs is a linking group.

5. The fluorescently detectable molecule of claim 5 wherein n and n' are each 1.

6. The fluorescently detectable molecule of claim 4 wherein Ar is phenyl and at least one of the n" Rs is a lower alkoxy.

7. The fluorescently detectable molecule of claim 4 wherein the M's comprise one or more metal ions including a rare earth metal ion in complex combination with the four carboxyl groups.

8. The fluorescently detectable molecule of claim 4 wherein the remainder of the molecule to which the pyridine moiety is linked is a biologically active material.

9. A fluorescently detectable molecule characterized as comprising a substituted aryl-substituted 2,6-bis[N,N-di(carboxyalkyl)aminoalkyl]pyridine moiety of the formula

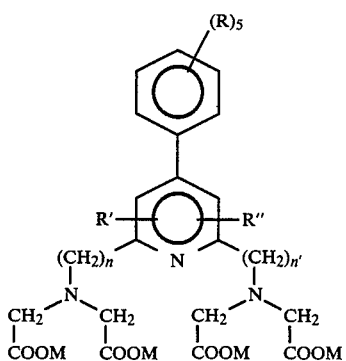

wherein M is hydrogen or metal ion, n and n' are independently the integers 1 or 2, the 5 Rs, R' and R" are each independently selected from a covalent bond, hydrogen and electron-releasing groups themselves selected from lower alkoxy, lower alkyl, amino, dialkylamino, aryl and aryloxy, subject to the proviso that at least one of the 5 Rs is an electron-releasing group and that at least one of R', R" and the n" Rs provides a link to the remainder of the molecule.

10. The fluorescently detectable molecule of claim 9 wherein one or more of the 5 Rs is an electron-releasing group.

11. The fluorescently detectable molecule of claim 10 wherein R' and R" are each hydrogens.

12. The fluroescently detectable molecule of claim 10 wherein and n' are each 1.

13. The fluorescently detectable molecule of claim 10 wherein the Ms are each hydrogens.

14. The fluorescently detectable molecule of claim 10 wherein the Ms comprise a rare earth metals ion in complex combination with the four carbonyl groups.

15. The fluorescently detectable molecule of claim 10 wherein the remainder of the molecule comprises a biologically active material.

16. A fluorescently detectable specific binding reagent having the structure

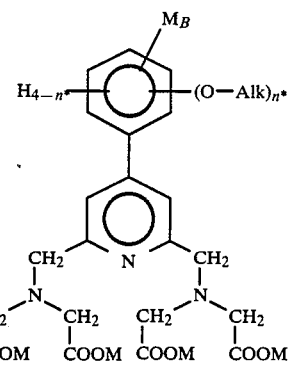

wherein M is metal ion or hydrogen n* is an integer from 1 to 4, Alk is a 1 to 4 carbon alkyl and $M_B$ is a biologically active material.

17. The reagent of claim 16 wherein each M is hydrogen.

18. The reagent of claim 16 wherein each M is metal ion.

19. The reagent of claim 16 wherein M comprises a rear earth metal ion in complex combination with the four carboxyl groups.

20. A substituted aryl-substituted 2,6-bis[N,N-di(carboxyalkyl)aminoalkyl]pyridine compound of the formula

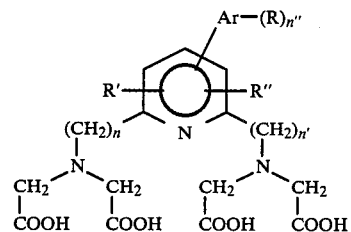

wherein n and n' are independently the integers 1 or 2 and R, R' and R" are independently selected from hydrogens, and electron-releasing groups themselves selected from lower alkoxies, lower alkyls, aminos, dialkylaminos, aryls and aryloxys, and Ar is an aryl, and n.' is an integer equal to the number of available bonding sites on Ar.

21. The compound of claim 20 wherein n and n' are each 1.

22. The compound of claim 21 wherein at least one of the R', R" and n Rs is an amine.

23. The compound of claim 22 wherein one of R', R" and the n Rs is an amine.

24. The compound of claim 20 wherein R and R" are hydrogens and Ar is phenyl such that the compound has the formula

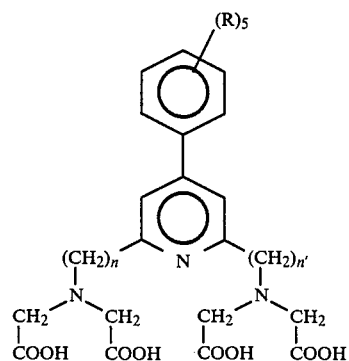

* * * * *